(12) United States Patent
Rosner

(10) Patent No.: US 7,106,830 B2
(45) Date of Patent: Sep. 12, 2006

(54) 3D X-RAY SYSTEM ADAPTED FOR HIGH SPEED SCANNING OF LARGE ARTICLES

(75) Inventor: S. Jeffrey Rosner, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 457 days.

(21) Appl. No.: 10/170,875

(22) Filed: Jun. 12, 2002

(65) Prior Publication Data

US 2003/0231739 A1 Dec. 18, 2003

(51) Int. Cl.
*G21K 5/10* (2006.01)
*G01N 23/04* (2006.01)

(52) U.S. Cl. ........................ 378/146; 378/57
(58) Field of Classification Search ............... 378/146, 378/119, 98.8, 98.11, 98.12, 58, 57, 90, 9, 378/98.9, 53
See application file for complete search history.

(56) References Cited

U.S. PATENT DOCUMENTS

| | | | | |
|---|---|---|---|---|
| 4,234,794 A * | 11/1980 | Voinea et al. | .................. | 378/12 |
| 4,942,596 A * | 7/1990 | Eberhard et al. | ........... | 378/109 |
| 5,966,422 A * | 10/1999 | Dafni et al. | .................... | 378/9 |
| 6,122,344 A * | 9/2000 | Beevor | ......................... | 378/88 |
| 6,151,381 A * | 11/2000 | Grodzins et al. | .............. | 378/90 |
| 6,185,271 B1 * | 2/2001 | Kinsinger | ...................... | 378/19 |
| 6,198,795 B1 * | 3/2001 | Naumann et al. | .............. | 378/57 |
| 6,272,230 B1 * | 8/2001 | Hiraoglu et al. | ............. | 382/100 |
| 6,380,540 B1 * | 4/2002 | Maor et al. | ............ | 250/363.04 |
| 6,421,420 B1 * | 7/2002 | Grodzins | .................... | 378/98.6 |
| 6,556,653 B1 * | 4/2003 | Hussein | ....................... | 378/90 |
| 6,600,805 B1 * | 7/2003 | Hansen | ........................ | 378/53 |

FOREIGN PATENT DOCUMENTS

| | | |
|---|---|---|
| EP | 0 173 047 A | 3/1986 |
| WO | 95 28715 A | 10/1995 |
| WO | 97 18462 A | 5/1997 |

* cited by examiner

*Primary Examiner*—Edward J. Glick
*Assistant Examiner*—Irakli Kiknadze

(57) ABSTRACT

A system for forming an image of an object. The system includes a first scanning x-ray source for generating x-rays that diverge from a source point along a first scan path, the point being variable and determined by an input signal provided by a controller. A plurality of x-ray detectors are positioned with respect to the first scan path and are readout by the controller. A conveyor moves the object relative to the first scanning x-ray source and the plurality of x-ray detectors. The object is divided into a plurality of voxels, and the x-ray detectors are positioned such that x-rays pass through each voxel and arrive at one of the detectors when the source point is located at a plurality of points along the first scan path. The controller preferably generates a three-dimensional representation of the object from the x-ray measurements.

19 Claims, 4 Drawing Sheets

3D X-RAY SYSTEM ADAPTED FOR HIGH SPEED SCANNING OF LARGE ARTICLES

FIELD OF THE INVENTION

The present invention relates to x-ray imaging systems, and more particularly, to x-ray imaging systems for generating three-dimensional views of large objects.

BACKGROUND OF THE INVENTION

The simplest form of x-ray imaging equipment utilizes projection imaging in which an object to be imaged is placed between an x-ray source and a two-dimensional x-ray recorder. Portions of the object that absorb or scatter x-rays are seen as a shadow on the image formed by the recorder. Unfortunately, these devices do not provide any information on the three-dimensional structure of the object. If the object contains a region of dense, x-ray absorbing material, the resultant "shadow" makes it difficult to see any other features that are between the x-ray source and the recorder for which the x-rays pass through the absorbing material.

This shortcoming of projection imaging is overcome by CT (computed tomography) scanners. CT scanners combine information from a variety of projection viewpoints to overcome the shadowing and generate a 3D (three-dimensional) description of the object. A typical CT system measures the x-ray flux reaching a detector from a source that moves around the object. The object being scanned is modeled by a plurality of voxels having unknown x-ray absorbency. At each point, the measured flux represents the weighted sum of the x-ray absorbencies of each voxel along the path from the x-ray source to the detector. Different paths provide weighted sums involving different sets of voxels. If sufficient points are measured, a data processing system can solve the resulting system of equations for the x-ray absorbency of each voxel. The resulting data can then be analyzed or displayed as a three-dimensional model of the object that can be viewed from different viewpoints.

CT scanners are widely used for imaging the human body as part of diagnostic procedures. In principle and in limited practice, such scanners would be useful in imaging inanimate objects such as passenger baggage that is to be placed on an aircraft. Unfortunately, the cost of this equipment and its relatively low throughput has inhibited the use of CT scanners for such high volume applications. A baggage scanning system must process tens of bags per minute. Because they utilize fan-beam imaging and only obtain information from a single 'slice' or two-dimensional voxel set for each revolution of the imaging system, conventional CT scanners require tens of seconds to scan a patient's chest; hence, such systems fall short of the required throughput. In addition, many bags are much larger than the human chest; hence, the scan times using conventional CT scanners would be even longer. As a result of the high capital cost and low throughput, the cost per 3D scan using conventional CT scanners is prohibitive. In addition, the large footprint and low throughput of conventional CT scanners require the dedication of large amounts of floor space, which further increases the cost of utilizing such systems.

Broadly, it is the object of the present invention to provide an improved scanning x-ray inspection system for the generation of three-dimensional information.

This and other objects of the present invention will become apparent to those skilled in the art from the following detailed description of the invention and the accompanying drawings.

SUMMARY OF THE INVENTION

The present invention is a system for forming an image of an object. The system includes a first scanning x-ray source for generating x-rays that diverge from a source point along a first scan path, the source point being variable and determined by an input signal provided by a controller. A plurality of x-ray detectors are positioned with respect to the first scan path and are readout by the controller. A conveyor moves the object relative to the first scanning x-ray source and the plurality of x-ray detectors. The object is divided into a plurality of voxels, and the x-ray detectors are positioned such that x-rays pass through each voxel and arrive at one of the detectors when the source point is located at a plurality of points along the first scan path. The controller preferably generates a three-dimensional representation of the object from the x-ray measurements. The first scanning x-ray source preferably includes first and second one-dimensional scanning x-ray tubes. The x-ray detectors are preferably constructed from a plurality of two-dimensional detector arrays. A second scanning x-ray source displaced from the first scanning x-ray source and generating x-rays that diverge from a source point along a second scan path can also be included in the system to improve throughput or selectively enhance the generated images based on the composition of the object.

DETAILED DESCRIPTION OF THE INVENTION

Figure 1:
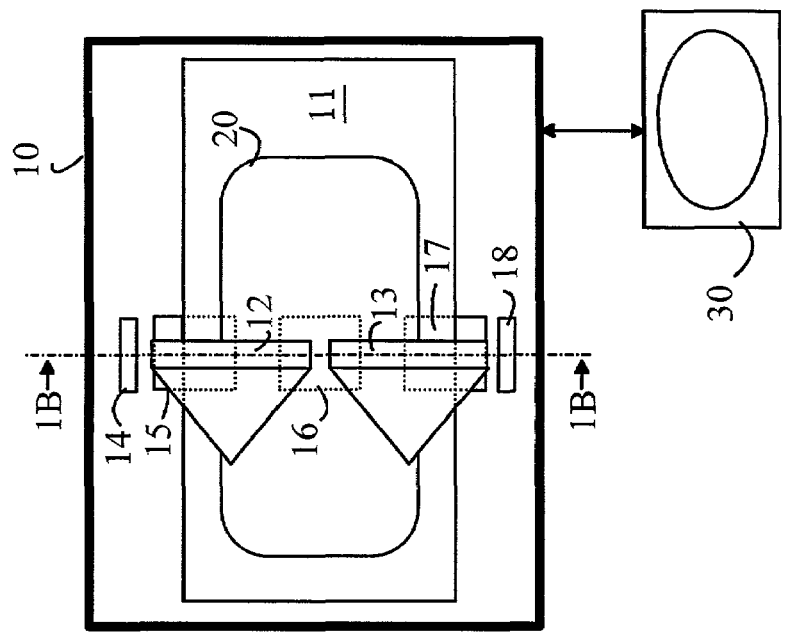
FIG. 1A is a top view of a scanner 10 for screening large objects such as suitcase 20.
FIG. 1B is a cross-sectional view of scanner 10 through line 1B—1B in FIG. 1A.

The manner in which the present invention provides its advantages can be more easily understood with reference to FIGS. 1A and 1B. FIG. 1A is a top view of a scanner 10 for screening large objects such as suitcase 20. FIG. 1B is a cross-sectional view of scanner 10 through line 1B—1B in FIG. 1A. Suitcase 20 moves through scanner 10 in a direction perpendicular to the plane of the figure on a conveyor 11.

Scanner 10 preferably utilizes one-dimensional scanning x-ray tubes to generate the x-ray flux used to scan the object. Conventional 2D x-ray scanning tubes are limited to scannable regions of the order of 10 cm in diameter because of difficulties associated with producing a sufficiently large x-ray transparent vacuum window. Large windows deflect under the vacuum and are easily broken. By reducing one dimension of the window to a small size, an arbitrarily long window can be created, allowing the application of such a technique to the inspection of large objects. To inspect an object that is moving, providing a small range of scanning in the second dimension allows the scanner to track the movement of the object on the conveyor. Such an arrangement would allow longer imaging times without blurring. In the following discussion, a "one-dimensional" scanning x-ray tube also includes two-dimensional tubes in which there is only a limited scanning range in the second direction. Any x-ray tube having a length to width scanning ratio of greater than five shall be deemed to be a one-dimensional scanning x-ray tube.

Figure 3:
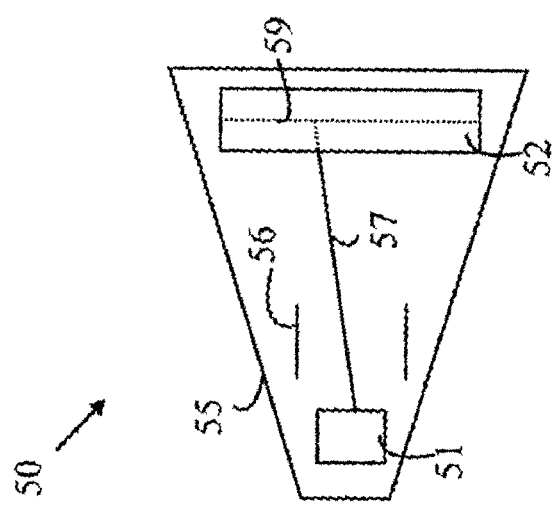

Two such one-dimensional scanning x-ray tubes are shown at 12 and 13. At any given time, each of the scanning x-ray tubes provides a point source of x-rays whose location can be moved along a substantially linear scan path as shown in FIG. 3 at 59. The positions along the scan path of the source point from which the x-rays radiate are controlled by a controller 30. X-rays are projected from the source point approximately isotropically (within the useful range). Such flux is limited by the extent of any windows used to provide an x-ray transparent port in the vacuum envelope to some conic section. The useful radiation, referred to as the 'x-ray cone beam' is defined by the intersection of the x-radiation from a given position of the source point with each of the image sensors. Each 2D image sensor, therefore, defines a pyramid-shaped 'x-ray cone'. Exemplary x-ray cones corresponding to the source point located at point 26 are shown at 25. X-rays from each position of the source point are used to generate a partial image of the object. In general, each position of the source point will generate x-rays that reach a number of the 2D-image sensors. The image data is preferably recorded by as many of the image sensors 14–18 as possible. The x-ray image sensors are preferably two-dimensional arrays of x-ray detectors. The data from the image sensors is read out by controller 30. To simplify the drawing, the connections from the controller to the x-ray sensors and x-ray tubes have been omitted from the drawing. Two-dimensional x-ray imaging arrays are available commercially from companies such as Varian, Kodak, and Trixell, and hence, will not be discussed in detail here.

The object being scanned is divided into voxels, i.e., small volume elements such as element 40 shown in FIG. 1B. As will be explained in more detail below, the x-ray sources and image detectors are positioned such that each voxel in the volume being scanned is intersected by rays extending between a plurality of combinations of source point position and image sensor pixel and contains absorption information about the intersected voxels. Hence, the collection of image sensor pixel measurements may be combined mathematically to generate the three-dimensional representation of the object in which each voxel is characterized by its x-ray absorption. The resulting model can be displayed on controller 30 from a variety of viewpoints to allow the operator to check for various weapons or hazardous materials such as explosives. Alternatively, the resulting model can be presented to software designed for decision analysis to allow the automated determination of a result; this could be a 'threat assessment' for the case of airport inspection.

As noted above, providing high throughput is a primary goal of commercial scanners for use in baggage screening. The use of scanning x-ray tubes substantially improves the throughput of the present invention relative to conventional CT scan systems in which the x-ray source and detector are fixed relative to one another but are physically moved around the object to be scanned. The use of multiple x-ray image sensors also improves the throughput of the system, since the individual image sensors can be read out in parallel into controller 30, thus reducing the data acquisition time. It should also be noted that this system is fully scalable in cost/performance ratio. Throughput can be increased by increasing the number of image sensors thereby increasing the number of voxels sampled for each position of the x-ray source point. The compactness of such a system additionally would allow further performance scaling by duplicating the x-ray source and detectors at a second location along the conveyor, as will be described further below.

Figure 2:
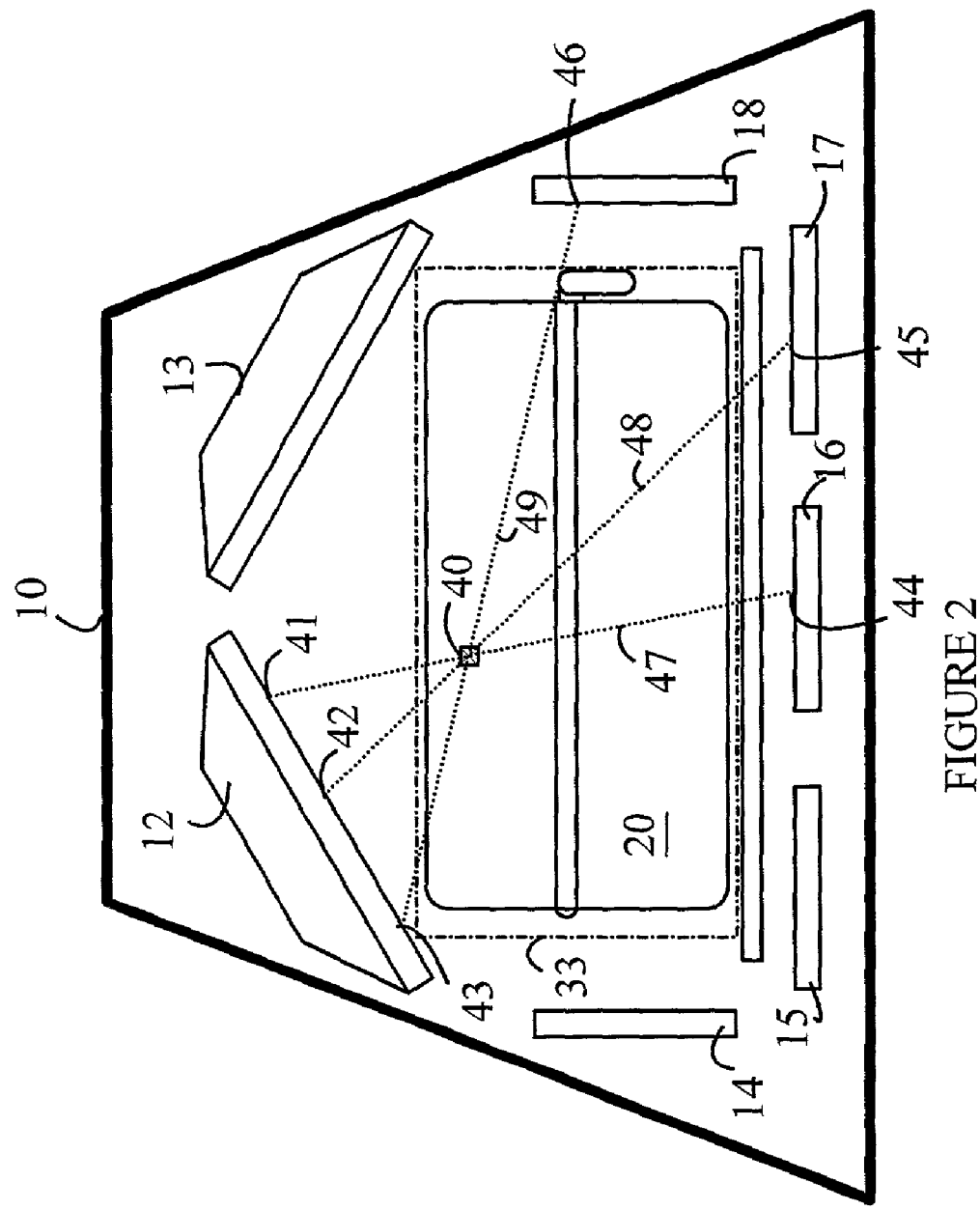
FIG. 2 is a cross-sectional view of scanner 10 through line 1B—1B illustrating the illumination of a voxel by x-rays generated at different points on one of the one-dimensional scanning x-ray tubes.

The use of a scanning x-ray tube having a scan path with a length that is of the same order of magnitude as the cross-sectional dimensions of the volume being scanned provides additional benefits, which can be more easily appreciated with reference to FIG. 2. FIG. 2 is the same cross-sectional view of scanner 10 as shown in FIG. 1B. Consider a voxel 40 in object 20, which occupies at least part of the volume 33 being scanned. Voxel 40 will be illuminated by x-rays generated at a number of different positions of the source point along the scan path of scanning x-ray tube 12. Three exemplary positions of the source point are shown at 41–43. X-rays generated at these source points and passing through voxel 40 are detected by pixels 44–46, respectively, on x-ray sensors 14–16, respectively. When the x-ray tube has its source point positioned at position 41, the pixel 44 measures a weighted sum of the absorbencies of the voxels along ray 47 including that of voxel 40. Similarly, when the source point is positioned at position 42, pixel 45 measures a weighted sum of the absorbencies of the voxels along ray 48 including that of voxel 40, and so on. Each measured value can be used to define an equation relating a weighted sum of the x-ray absorbency of the voxels on that ray to the measured value. In principle, this system of equations can be solved for the individual x-ray absorbency of each of the voxels provided enough independent measurements are made.

Since the dimensions of the scan path of one-dimensional scanning x-ray tube 12 are of the same order as those of the cross-sectional dimensions of the volume being scanned, which is occupied at least in part by object 20, the angles with which the various rays pass through voxel 40 from different positions of the source point along the scan path varies greatly as the source point moves along the scan path. Hence, x-ray absorbency of voxel 40 is measured in weighted sums that differ markedly as the source point moves. In contrast, if the scan path or scan area of the scanning x-ray tube had linear dimensions substantially smaller than the cross-sectional dimensions of the volume being scanned, each time voxel 40 was measured in a weighted sum, the weighted sum would also include the same neighboring voxels. In this case, the system of equations would not be as well conditioned and a solution would be difficult, if not impossible. To provide the advantages discussed above, the length of the scan path along which the source point of the scanning x-ray tube moves during the scan is preferably at least 25% of the largest cross-sectional dimension of the volume being scanned in a plane that includes the scan path and at least one of the image sensors.

Also, as noted above, equipment cost is a primary factor in commercial scanning equipment. The use of multiple x-ray image sensors substantially reduces the equipment costs. Scanners for baggage screening must accommodate objects that are 60 to 100 cm across. If a single large x-ray image sensor were utilized to provide the data collection, the dimensions of the image sensor would need to be of the order of 100 cm. There is an optimum cost/pixel in the x-ray image sensors that depends on the size of the image sensor. Very large image sensors become quite expensive because of poor yield in the fabrication process. Likewise, very small image sensors are not a cost-effective solution for covering large areas.

In the preferred embodiment of the present invention, the x-ray image sensors are mounted in a plurality of orientations. For example, image sensors 14 and 18 are oriented at right angles to image sensors 15–17 in the arrangement shown in FIG. 1B. Ideally, each pixel in each of the image sensors would be illuminated by x-rays that strike the pixel at 90 degrees with respect to the plane of the image sensor for each possible position of the source point along the scan path of each of the scanning x-ray tubes. This arrangement would maximize the flux intercepted by each pixel in the image sensors. It is difficult to provide an image sensor arrangement that meets this ideal criterion. By providing image sensors having different spatial orientations, the present invention provides a better approximation to this ideal situation than would be obtained if the image sensors all had the same orientation relative to the scan paths of the x-ray tubes. While the preferred embodiments of the present invention utilize image sensors that are planar, other image sensor configurations can be utilized.

The present invention is based, in part, on the observation that the image sensors do not need to "tile" the entire area under and around the volume being scanned. As long as each voxel in the volume is "seen" in a sufficient number of different source point/pixel combinations, the x-ray absorbency of that voxel can be computed. It can be shown that this can be accomplished with an arrangement that has spaces between the individual x-ray image sensors. In addition to allowing more optimal image sensors to be utilized, this feature of the present invention also provides scalability since image sensor pixels can be added in modular amounts to increase throughput.

Figure 4:
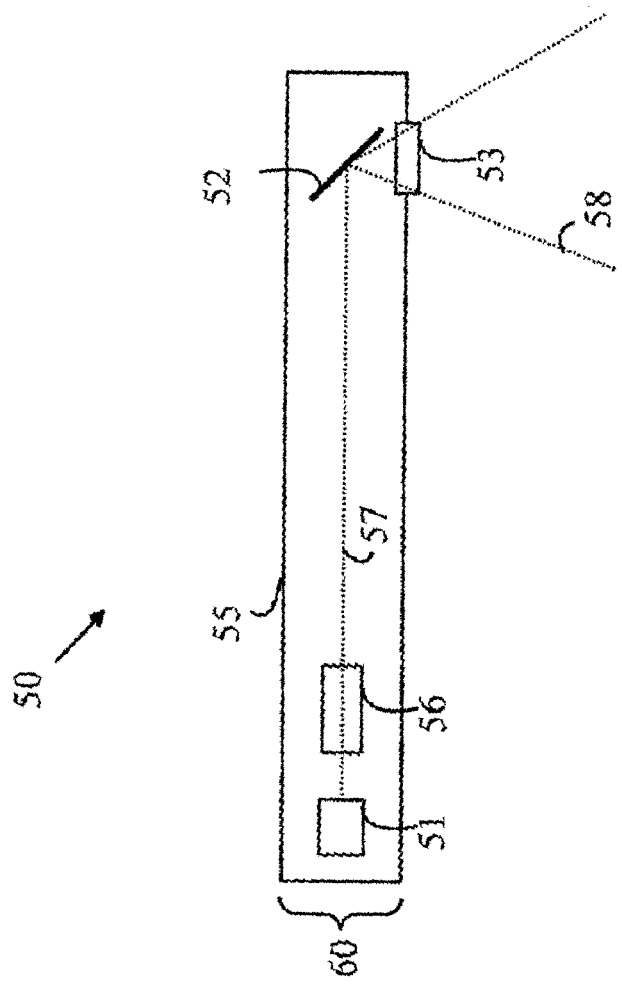
FIGS. 3 and 4 are top and side views, respectively, on a one-dimensional scanning x-ray tube 50.

The use of linear scanning x-ray sources also substantially reduces the equipment cost. Large-scale two-dimensional scanning x-ray tubes are very costly. Such tubes require large x-ray transparent windows and large evacuated structures that substantially increase the size of the scanner. Refer now to FIGS. 3 and 4, which are top and side views, respectively, on a one-dimensional scanning x-ray tube 50. Scanning x-ray tube 50 operates by accelerating electrons in an electron beam 57 from an electron source 51 into a metallic target 52, typically of W or Cu. The x-rays in cone 58 are used to illuminate the object located in the volume being scanned. These x-rays leave the target via the same surface through which the electron beam entered the target. These x-rays exit the x-ray tube via a narrow x-ray transparent window 53. An electron deflection circuit 56 determines the location at which the electron beam strikes the target and thus the source point of the x-rays. The deflection circuit may utilize magnetic or electrostatic fields to deflect the electron beam along the scan path. X-ray tube 50 is enclosed in a vacuum chamber 55. Window 53 and target 52 are preferably rectangular in shape, with a length to width ratio of at least 5 to 1. However, other elongate shapes may be utilized. It should also be noted that the actual shape of the target is not critical here, since window 53 determines the shape of the x-ray cone.

Since x-ray tube 50 is a one-dimensional scanning x-ray source, vacuum chamber 55 can be very narrow in dimension 60; hence, the x-ray tube is much more compact than two-dimensional x-ray tubes. In addition, by utilizing the "reflected" x-rays, the tube can be structured such that the vacuum chamber does not extend significantly beyond the target in the direction perpendicular to the electron beam. Hence, the overall dimensions of the scanner in which the one-dimensional scanning x-ray tubes are used are significantly smaller than a scanner based on a two-dimensional scanning x-ray tube. However, other designs of scanning x-ray tubes can be used. For example, if higher resolution is required for smaller objects, a transmission-type tube, where the x-ray window is also the x-ray producing target, can be used to allow closer spacing of the object to the x-ray source point.

Figure 5:
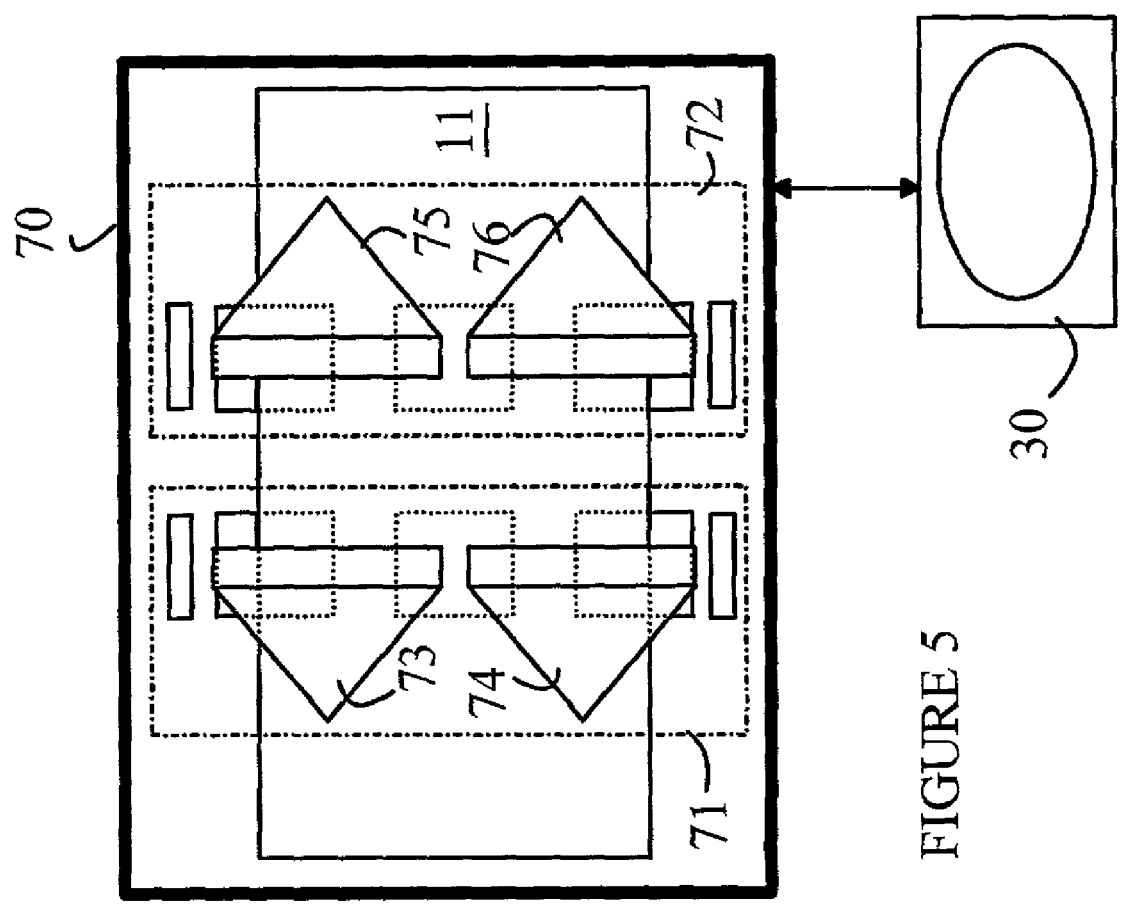
FIG. 5 is a top view of a scanning station 70 according to another embodiment of the present invention.

The above-described embodiments of the present invention utilize a single imaging station. However, embodiments having multiple imaging stations may also be utilized. Such an embodiment is shown in FIG. 5, which is a top view of a scanner 70 according to another embodiment of the present invention. Scanner 70 has two scanning stations, which are shown at 71 and 72. Each scanning station is similar to the scanning stations described above. The compact nature of the one-dimensional scanning x-ray tubes facilitates the construction of such multiple station scanners.

The additional scanning stations can increase the throughput of the scanner. In such arrangements, each scanning station can image a different section of the object, or the second scanning station can be rotated about the direction of travel of the conveyor with respect to the first station to increase the range of projection viewpoints that can be accumulated. This will increase the quality of the result. Since each station only needs to gather half of the projected views of the object (assuming some fixed minimum adequate number of projections required for the 3D information), the conveyor speed can be increased. The conveyor speed is only limited by the relationship between the conveyor speed, the required integration time for image acquisition, and the desired resolution. Controller 30 will compute the 3D description by combining the data from the two scanning stations.

The additional scanning station can also be utilized to provide data for enhancing the images based on the elemental composition of the object being scanned. In such embodiments, the x-ray spectrum generated by the scanning x-ray tubes differs between the stations. That is, x-ray tubes 73 and 74 shown in FIG. 5 generate x-rays having a first energy spectrum and x-ray tubes 75 and 76 generate x-rays having a second energy spectrum. The energy spectrums can be altered by changing the acceleration voltage in the tubes or by providing an appropriate absorption filter in front of one set of x-ray tubes. Hence, each station forms an image of the object using a different energy spectrum. The two images can then be combined to provide a single image that is enhanced for a particular range of elements. If sufficient stations are included, images based on specific elements can be generated.

Similarly, the x-ray image sensors utilized in the different stations can have different energy sensitivities. The different images constructed from such sensor arrays can also be combined to provide images that are enhanced for a particular elemental range.

The above-described embodiments of the present invention have utilized a conveyor belt for moving the object relative to the scanning station. However, embodiments in which the object remains stationary and the scanning station moves may also be practiced. Such embodiments are useful when the volume being scanned is much larger than the scanning station. For example, a scanner for scanning cargo containers and the like before loading or after unloading may be more economically constructed if the scanner moves and the large container remains fixed. Such embodiments, however, are not preferred in situations such as baggage screening in which the baggage is already moving on a conveyor. It will also be apparent that other actuators for moving the object to be scanned relative to the scanning station may also be utilized. Accordingly, the term "conveyor" is defined to include any mechanism for moving the object to be scanned relative to the x-ray source and detectors.

The above-described embodiments of the present invention have been described in terms of scanning volume that is fixed by the dimensions of the x-ray tubes and the image sensors. This volume represents the largest volume for which a 3D representation of an object can be generated. However, embodiments in which smaller volumes are scanned based on estimates of the object size can also be practiced. In such embodiments, the volume actually occupied by an object can be estimated during an initial scan of the object by an optical scanner.

Various modifications to the present invention will become apparent to those skilled in the art from the foregoing description and accompanying drawings. Accordingly, the present invention is to be limited solely by the scope of the following claims.

What is claimed is:

1. A system for forming an image of an object located in a volume being scanned, said system comprising:
    a stationary first scanning x-ray source for generating x-rays that radiate from a first source point located along a first scan path, said first source point being movable along said first scan path in response to an input signal;
    a plurality of x-ray image sensors positioned to intercept said x-rays after passing through said volume, said x-ray image sensors comprising a two-dimensional array of x-ray sensors; and
    a controller for generating said input signal and receiving signals from said x-ray image sensors,
    wherein said object is divided into a plurality of voxels and wherein said x-ray image sensors are positioned such that x-rays pass through each voxel and arrive at one of said image sensors when said fast source point is located at a plurality of locations along said first scan path, the number of said locations along said first scan path being sufficient to generate a three-dimensional representation of said object.

2. The system of claim 1 further comprising a conveyor for moving said object relative to said first scanning x-ray source and said plurality of x-ray image sensors.

3. The system of claim 2 wherein said first scanning x-ray source and said plurality of x-ray image sensors are fixed relative to one another.

4. The system of claim 1 wherein said two-dimensional array of
    x-ray image sensors is planar.

5. The system of claim 1 wherein said x-ray image sensors comprise a plurality of two-dimensional arrays of x-ray sensors, and wherein said two-dimensional arrays of x-ray image sensors are separated by spaces.

6. The system of claim 1 wherein said plurality of x-ray image sensors comprise a first planar two-dimensional array of x-ray image sensors having a first orientation relative to said first scanning x-ray source and a second planar two-dimensional array of x-ray image sensors having a second orientation relative to said first scanning x-ray source, said first and second orientations being different from one another.

7. The system of claim 6 wherein said fast planar two-dimensional array of x-ray image sensors is oriented at right angles to said second planar two-dimensional array of x-ray image sensors.

8. A system for forming an image of an object located in a volume being scanned, said system comprising:
    a first scanning x-ray source for generating x-rays that radiate from a first source point located along a first scan path, said first source point being movable along said first scan path in response to an input signal;
    a plurality of x-ray image sensors positioned to intercept said x-rays after passing through said volume; and
    a controller for generating said input signal and receiving signals from said x-ray image sensors,
    wherein said object is divided into a plurality of voxels and wherein said x-ray image sensors are positioned such that x-rays pass through each voxel and arrive at one of said image sensors when said first source point is located at a plurality of locations along said first scan path; and
    wherein said scan path includes a first point and a second point said first and second points being separated by a distance greater than 25% of the largest cross-sectional dimension of said volume being scanned, said cross-section being taken through said volume in a plane comprising said first scan path and at least one of said x-ray sensors.

9. The system of claim 1 wherein said controller generates a three-dimensional representation of said object.

10. A system for forming an image of an object located in a volume being scanned, said system comprising:
    a first scanning x-ray source for generating x-rays that radiate from a first source point located along a first scan path, said first source point being movable along said first scan path in response to an input signal;
    a plurality of x-ray image sensors positioned to intercept said x-rays after passing through said volume, said x-ray image sensors comprising a two-dimensional array of x-ray sensors; and
    a controller for generating said input signal and receiving signals from said x-ray image sensors,
    wherein said object is divided into a plurality of voxels and wherein said x-ray image sensors are positioned such that x-rays pass through each voxel and arrive at one of said image sensors when said first source point is located at a plurality of locations along said first scan path, the number of said locations along said first scan path being sufficient to generate a three-dimensional representation of said object,
    wherein said first scanning x-ray source comprises a one-dimensional scanning x-ray tube.

11. A system for forming an image of an object located in a volume being scanned, said system comprising:
    a stationary first scanning x-ray source for generating x-rays that radiate from a first source point located along a first scan path, said first source point being movable along said first scan path in response to an input signal;
    a plurality of x-ray image sensors positioned to intercept said x-rays after passing through said volume; and
    a controller for generating said input signal and receiving signals from said x-ray image sensors,
    wherein said object is divided into a plurality of voxels and wherein said x-ray image sensors are positioned such that x-rays pass through each voxel and arrive at one of said image sensors when said first source point is located at a plurality of locations along said first scan path;
    said system further comprising a stationary second scanning x-ray source displaced from said first scanning x-ray source and generating x-rays that diverge from a second source point located along a second scan path, said second scanning x-ray source generating x-rays having a different energy spectrum than said x-rays generated by said first scanning x-ray source.

12. A method for forming an image of an object located in a volume being scanned, said method comprising:
for each of a plurality of source point locations along a first scan path on a target in a linear x-ray tube, generating x-rays having a first energy spectrum that radiate into said volume from that source point; and generating image data at a plurality of imaging locations in a two-dimensional array of locations from said generated x-rays; and
combining said generated image data to provide a three-dimensional representation of said object, wherein each source point location is at a different relative position with respect to said plurality of imaging locations.

13. The method of claim 12 further comprising moving said object relative to said first scan path.

14. The method of claim 12 wherein said x-rays are generated by a one-dimensional scanning x-ray tube.

15. The method of claim 12 wherein said imaging locations are defined by a plurality of x-ray image sensors, each x-ray image sensor comprising a two-dimensional array of x-ray detectors.

16. The method of claim 15 wherein said plurality of x-ray image sensors comprises a first x-ray image sensor having a first orientation relative to said first scanning x-ray source and a second x-ray image sensor having a second orientation relative to said first scan path, said first and second orientations being different from one another.

17. The method of claim 16 wherein said first x-ray image sensor is oriented at right angles to said second x-ray image sensor.

18. A method for forming an image of an object located in a volume being scanned, said method comprising:
for each of a plurality of source point locations along a first scan path in a stationary x-ray source, generating x-rays having a first energy spectrum that radiate into said volume from that source point; and generating image data at a plurality of imaging locations from said generated x-rays; and
combining said generated image data to provide a three-dimensional representation of said object, wherein each source point location is at a different relative position with respect to said plurality of imaging locations; wherein
said first scan path includes a first point and a second point, said first and second points being separated by a distance greater than 25% of the largest cross-sectional dimension of said volume, said cross-section being taken through said volume in a plane comprising said first scan path and an x-ray sensor image sensor.

19. A method for forming an image of an object located in a volume being scanned, said method comprising:
for each of a plurality of source point locations along a first scan path in a first stationary x-ray source, generating x-rays having a first energy spectrum that radiate into said volume from that source point; and generating image data at a plurality of imaging locations from said generated x-rays;
combining said generated image data to provide a three-dimensional representation of said object, wherein each source point location is at a different relative position with respect to said plurality of imaging locations;
generating x-rays having a second energy spectrum that radiate into said volume from a plurality of source points along a second scan path in a second stationary x-ray source; and generating image data from a plurality of imaging locations from said generated x-rays having said second energy spectrum, said first energy spectrum being different from said second energy spectrum.

* * * * *

UNITED STATES PATENT AND TRADEMARK OFFICE
CERTIFICATE OF CORRECTION

| | |
|---|---|
| PATENT NO. | : 7,106,830 B2 |
| APPLICATION NO. | : 10/170875 |
| DATED | : September 12, 2006 |
| INVENTOR(S) | : Rosner |

Page 1 of 1

It is certified that error appears in the above-identified patent and that said Letters Patent is hereby corrected as shown below:

On the face page, in field (56), under "U.S. Patent Documents", in column 2, line 6, after "6,556,653" delete "B1" and insert -- B2 --, therefor.

On the face page, in field (56), under "U.S. Patent Documents", in column 2, line 7, after "6,600,805" delete "B1" and insert -- B2 --, therefor.

In column 7, line 36, in Claim 1, delete "fast" and insert -- first --, therefor.

In column 7, line 62, in Claim 7, delete "fast" and insert -- first --, therefor.

Signed and Sealed this

Twenty-ninth Day of April, 2008

JON W. DUDAS
*Director of the United States Patent and Trademark Office*